United States Patent [19]

Lautenschläger

[11] Patent Number: 5,270,010
[45] Date of Patent: Dec. 14, 1993

[54] SAMPLE HOLDER FOR DECOMPOSITION OR ANALYSIS OF SAMPLE MATERIALS

[76] Inventor: Werner Lautenschläger, Waldstrasse 15, D-7970 Leutkirch, Fed. Rep. of Germany

[21] Appl. No.: 713,074

[22] Filed: Jun. 11, 1991

[30] Foreign Application Priority Data

Jun. 13, 1990 [DE] Fed. Rep. of Germany ....... 4018955
May 3, 1991 [EP] European Pat. Off. ....... 91-107-194.2

[51] Int. Cl.$^5$ .............................................. B01L 3/00
[52] U.S. Cl. .................................. 422/102; 422/103; 422/104; 220/209
[58] Field of Search ................. 422/102, 99, 103, 104; 219/8.5, 10.55 A, 10.57, 10.73; 220/209

[56] References Cited

U.S. PATENT DOCUMENTS

| | | | |
|---|---|---|---|
| 3,179,122 | 4/1965 | Wasdell | 220/209 |
| 3,265,296 | 8/1966 | Mitchell | 494/16 |
| 3,459,369 | 8/1969 | Marks | 494/16 |
| 4,079,854 | 3/1978 | Shaw et al. | 230/89 |
| 4,151,253 | 4/1979 | Waggoner et al. | 422/102 |
| 4,168,012 | 9/1979 | Hawkinson | 220/209 |
| 4,342,419 | 8/1982 | Conway | 494/20 |
| 4,672,996 | 6/1987 | Floyd et al. | 137/522 |
| 4,689,306 | 8/1987 | Redikultsev et al. | 422/103 |
| 4,690,670 | 9/1987 | Nielsen | 422/102 |
| 4,752,445 | 6/1988 | Zell | 422/103 |
| 4,882,128 | 11/1989 | Hukvari et al. | 422/119 |
| 4,944,425 | 7/1990 | Kasugai | 220/209 |
| 4,944,923 | 7/1990 | Heinrichs et al. | 422/102 |
| 4,993,602 | 2/1991 | Casey | 220/209 |

FOREIGN PATENT DOCUMENTS

| | | |
|---|---|---|
| 2706723 | 2/1978 | Fed. Rep. of Germany . |
| 3620381 | 1/1989 | Fed. Rep. of Germany . |
| 3818697 | 12/1989 | Fed. Rep. of Germany . |
| 3839901 | 5/1990 | Fed. Rep. of Germany . |
| 2227186 | 7/1990 | United Kingdom . |

*Primary Examiner*—Robert J. Warden
*Assistant Examiner*—Hien Tran
*Attorney, Agent, or Firm*—Fitzpatrick, Cella, Harper & Scinto

[57] ABSTRACT

In a sample holder (9) for decomposition or analysis of sample material by heating the sample material in a heating appliance (1) such as a microwave oven, comprising a receiving part (11) having a filling opening (15) for the sample material, a lid (14) to close the receiving part (11) and a valve (16) in the upper part of the sample holder (9) that comprises a valve seat and a valve member that bears, counter to its direction of closure, against an elastically yielding thrust piece (31), the cross-section of the thrust piece (31) in the plane running in the direction of closure of the valve (16) is shaped as a plate spring.

17 Claims, 3 Drawing Sheets

SAMPLE HOLDER FOR DECOMPOSITION OR ANALYSIS OF SAMPLE MATERIALS

TECHNICAL FIELD OF THE INVENTION

The invention relates to a sample holder for decomposition or analysis of a sample material during heating thereof.

BACKGROUND OF THE INVENTION AND PRIOR ART

In a sample holder of this kind one or more materials are simultaneously subjected, for the purpose of decomposition or analysis, to chemical treatment in which heat may be supplied to promote the reaction An example of a sample material to be investigated is sewage sludge that is to be decomposed with highly aggressive acids. To accelerate the decomposition, i.e. the chemical process, it is usual to heat the sample material with the addition of acids or other decomposition agents by heating the sample holder with the sample material and the decomposition agent in a heating appliance, preferably by subjecting it to microwave radiation in a microwave oven.

The heating can result in a large excess pressure in the sample holder. To prevent damage to or explosion of the sample holder a valve is provided in an outlet opening that automatically opens if a predetermined internal pressure is exceeded.

In German patent application 38 39 901 a sample holder of the above-mentioned kind is described that comprises a bottom container part with a pot-shaped cylindrical lid that can be screwed in an inverted position on to the pot-shaped cylindrical bottom container part. In this arrangement the valve forms an integral part of a valve body that can be screwed on to a connecting piece that is located centrally on the lid and incorporates the outlet opening. The valve is situated in an outlet passage that passes through the valve body and includes a conical valve seat against which a valve member having a corresponding conical head can be prestressed from above by an amount such that when the internal pressure in the sample holder reaches a predetermined value the valve member lifts off under this internal pressure and frees the outlet opening. The valve member can move vertically in a plug that can be screwed from above into an open-topped recess in the valve body. The prestressing of the valve member is done through a thrust piece of elastic material, preferably silicone, that is located between the valve member and the plug. The plug can be screwed into the valve body in the manner of a press screw, by means of a turning member at its upper end, until the elastic thrust piece is compressed, thereby producing the prestressing force. The depth to which the plug is screwed in, and thus the prestressing force, can be determined by means of indicating marks on the valve body and/or on the turning member.

This known arrangement has proved to be practicable and useful. However, it is complicated and expensive to manufacture, since a special valve housing has to be made and fitted. The valve housing seated on the lid, or the valve body, also increases the height of the sample holder. Screwing the additional valve housing or valve body on and off is also regarded as a time-consuming operation. Apart from this, screw threads on the top and bottom parts of the container are expensive and make manipulation slow and difficult. Furthermore thick walls are necessary, leading to long cooling times and increased material requirements and weight. There is also a risk of damage to the sample holder by distortion and ageing, particularly in the region of the screw threads and with long decomposition times.

The heating of the sample material in the sample holder is preferably done in a microwave oven, in which several sample holders can be heated at the same time. To ensure uniformity of heating a rotary stand is provided in the oven on which the sample holders can be rotated about a vertical axis.

To provide resistance to the corrosive acids that can be generated in the course of the decomposition and to make microwave heating possible a chemically inert material that is transparent to microwaves is required. For this purpose a heat-resistant and chemically inert plastic material is very suitable.

In an arrangement known from DE-B-36 20 381, having a pot-shaped receiving part with a lid in the form of a disc resting on its rim, the valve member is formed by the lid itself and a flat bearing disc of aluminum is arranged on the lid. To use a sample holder with a valve constructed in this way for the decomposition of sample material requires not only a stand in the oven but also a retaining means extending over the sample holder to hold the lid in its closed position. For this purpose a base plate is provided beneath the sample holder and a retaining plate that extends over it, the retaining plate having a press screw arranged to be screwed into it from above and coaxially with the sample holder so that its lower end presses vertically against the bearing disc and thus holds the valve in its closed position. Under excess internal pressure in the sample holder the lid can distort slightly and rock about the press screw. Oscillatory bending upwards of the lid will clearly occur in some position at its periphery. DE-B-36 20 381 does not say whether or not the bearing disc participates in this movement of the lid. It must be assumed that the aluminum bearing disc will likewise bend upwards and outwards under the increased internal pressure at some position on the periphery, so that the lid follows this movement and the excess pressure can blow off through the resulting gap. The internal pressure will obviously always seek out the weakest peripheral position on the lid and/or the bearing disc. At any rate, what will happen is a very indefinite opening, since both in the case of one lid in this peripheral region and also when there is more than one lid (simultaneous heating of several sample holders) blowing off will occur at different internal pressures as a result of differences in the bending strength of the lid or lids. This is undesirable, since at uncontrolled different internal pressures different decomposition reactions can occur and thus falsify the results of the decomposition or the analysis. With this known arrangement there is also the danger that the aluminum bearing disc may be permanently deformed either on screwing up the press screw or by the internal pressure, thus impairing the functioning of the sample holder through premature opening or making it unusable. A further disadvantage is that this known arrangement is not suitable for heating in a microwave oven.

OBJECT OF THE INVENTION

It is an object of the invention to improve the functional stability of a sample holder of the abovementioned kind.

SUMMARY OF THE INVENTION

In the sample holder of the invention according to one aspect of the present invention, the thrust piece is in the form of a plate spring. As a result of this form the thrust piece is mainly subjected to bending stresses, and not to compression. This enables substantially uniform elasticity characteristics to be obtained both for one thrust piece of a single sample holder and also for a plurality of thrust pieces of a plurality of sample holders, so that the stress exerted on the valve by the thrust piece can be more easily controlled and determined. It is thus simpler to make thrust pieces having substantially uniform elasticity characteristics.

A further advantage of the sample holder of the invention according to this aspect of the invention is that it makes it simpler to achieve both a small sectional size for the thrust piece and greater spring force, and in addition a greater spring excursion of the thrust piece. The latter is important from the point of view of manipulation, namely in the screwing up of the pressure screw of the retaining means against the lid. When a larger spring excursion is available, any differences in pressure that may occur will have less effect on the opening pressure, since smaller differences in closure forces can be obtained. Larger differences in closure forces would lead to there being different opening pressures, which is undesirable. It is particularly advantageous if the compliance of the thrust piece follows a characteristic curve that does not increase. Compliance of this kind is comparable with a weight, which always exerts the same force irrespective of the distance travelled. With an arrangement of this kind the operator does not have to pay attention to the tension or torque with which the press screw is prestressed against the lid. Even if the press screw were to be screwed in rather more than necessary this would not lead to any increase in the closure force, owing to the non-rising characteristic curve. Consequently the thrust piece always exerts substantially the same closure force irrespective of how much it is pre-stressed by the press screw, so that the respective valve will always open at the same opening pressure. Permanent deformation of the thrust piece is avoided and long life is achieved.

In the sample holder of the invention according to another aspect of the invention, the valve is stabilised by the presence of the dimensionally stable insert. This gives the manufacturer freedom of choice in respect of the material for the lid, so that he can use a softer and-/or less heat-resistant or chemically inert and less dimensionally stable material for it. A particularly suitable material for the lid is a PTFE derivative or Teflon, which is relatively soft particularly at higher temperatures. This is unimportant, since the dimensional stability of the insert replaces that of the lid. The dimensional stability is thus maintained, so that the elasticity of the thrust piece acts substantially without distortion, which is a further reason why the valve will always open at a definite, and preferably constant, opening pressure.

The thrust piece preferably consists of a hard or viscoelastic plastics material, for example HTC (high temperature compound) plastic.

In the sub-claims advantageous features are set forth that contribute to the achievement of the present objects and give embodiments that are simpler, cheaper and smaller and also enable different opening pressures of particular orders of magnitude to be obtained should this be desired.

BRIEF DESCRIPTION OF THE DRAWINGS

The invention will now be described in more detail by way of example with reference to the accompanying drawings, in which.

DETAILED DESCRIPTION OF PREFERRED EMBODIMENTS OF THE INVENTION

Figure 1:
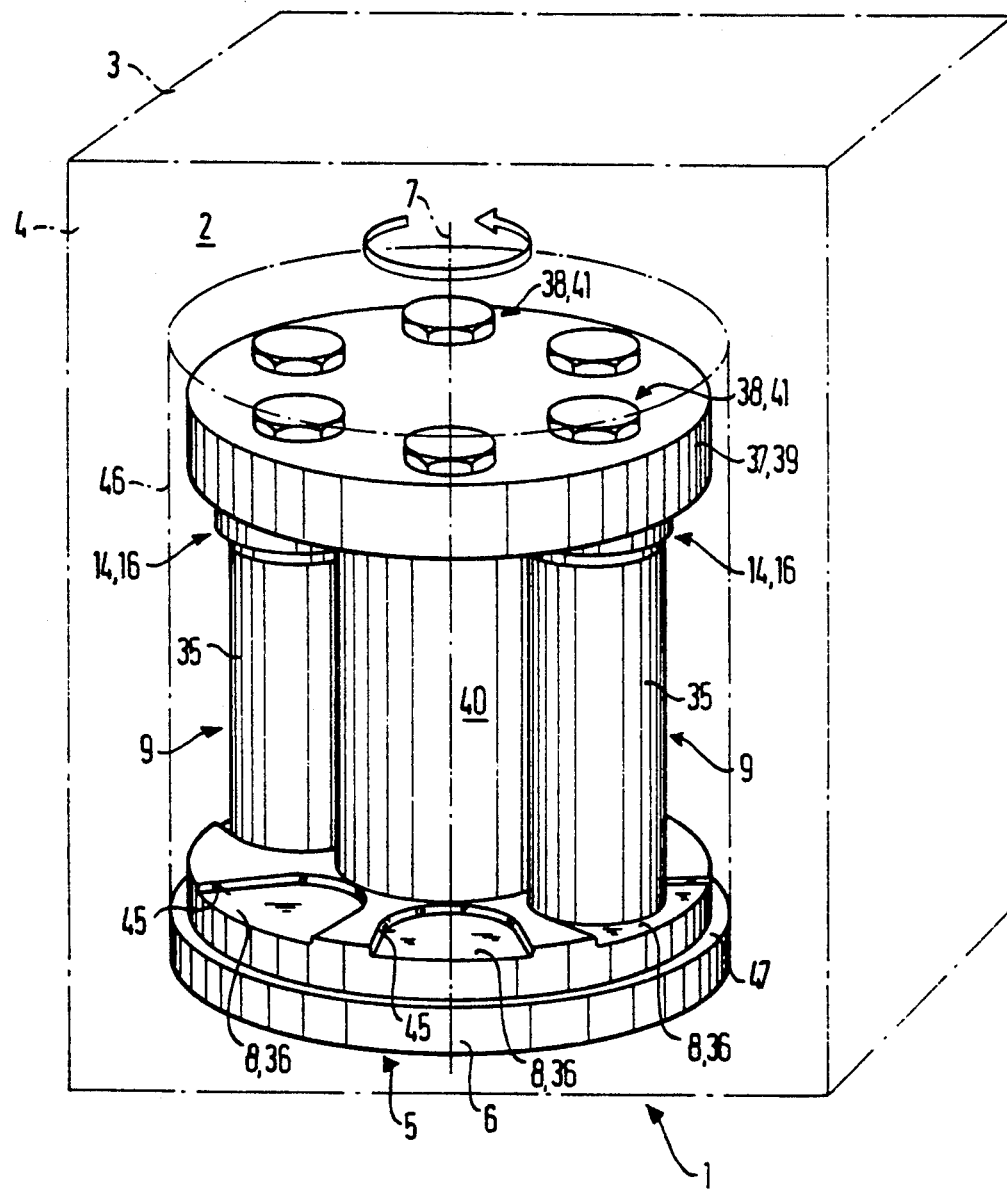
FIG. 1 shows a perspective view of a simplified heating appliance with a carrier for sample holders for decomposition or analysis of sample material.

The heating appliance 1 is a microwave oven having a housing 3 with a door 4 on its front face, enclosing a heating chamber 2. In the bottom part of the heating chamber 2 is the carrier 5, preferably in the form of a round plate 6, that can rotate about a vertical axis 7. On the carrier 5, and preferably distributed uniformly around a pitch circle, there are positions 8 for placing or standing sample holders 9, one to each position In the present embodiment six positions 8 are provided for six sample holders 9, two of which are shown opposite to one another.

The sample holders 9 are preferably all of the same form, each consisting of a pot-shaped housing 11 having a circular horizontal cross-section with a horizontal base 12 and a cylindrical wall 13 extending vertically and having a flanged rim 13a. The opening 15 of the housing, which can be closed by a lid 14, is bounded by the upper internal rim of the wall 13.

The sample holder 9 is provided in its upper part with a valve 16 that opens automatically when a predetermined internal pressure in the sample holder 9, which is subjected to the action of heat during decomposition of a sample material contained in it, is exceeded, so that the internal pressure can escape to the exterior and be reduced. This serves to prevent the internal pressure from exceeding a predetermined value and overloading the sample holder 9 or even causing it to explode. The valve member of the valve 16 is the lid 14 itself.

The valve seat of the valve 16 is formed on the upper rim of the cylindrical wall 13 of the housing and comprises the upper concentric, radially annular rim surface 18 of the cylindrical wall 13 and the rim flange 13a thereof. The lid 14 has, on the outer periphery of its underside, a correspondingly shaped radial, annular sealing surface 19. The diameter of the disc-shaped lid 14 corresponds approximately to, and may be slightly larger than, the external diameter of the housing 11. The lid 14 also has on its underside a centering projection 14a which fits into the housing 11. The horizontal lower surface of this projection is designated 21. Concentrically on the top of the lid 14 there is a circular recess 22 with a flat, radial bottom surface 23. For safety the lid 14 is provided in the middle with a rated break point 24, preferably formed by a weakening of the disc-shaped lid 14, for example in the form of an annular groove or a central blind hole 25, preferably located in the top of the lid 14.

On top of the lid 14 there is a disc-shaped insert 27 which is inserted into and substantially fills the recess 22 with its radial bottom surface resting on the bottom surface 23 of the recess 22 and its peripheral surface preferably likewise in contact with the hollow cylindrical internal wall of the recess 22. The diameter of the circular insert 27 is such that it projects beyond the inner edge of the rim surface 18, and may correspond approximately to the external diameter of the housing wall 13 or of the rim flange 13a. The insert 27 may however have a larger diameter than the housing 11. On the top of the insert 27 and concentric therewith there is a circular recess 28 with a flat, radial bottom surface 29.

Each sample holder 9 is provided with a disc-shaped, elastic thrust piece 31 that is inserted into the recess 28 on the lid 14 for the functional operation of the sample holder 9. Because of its elasticity the thrust piece allows the valve 16 to be prestressed by a definite amount. The thrust piece 31 is located outside the sample holder 9, and hence in a cold region around which air can circulate.

Figure 2:
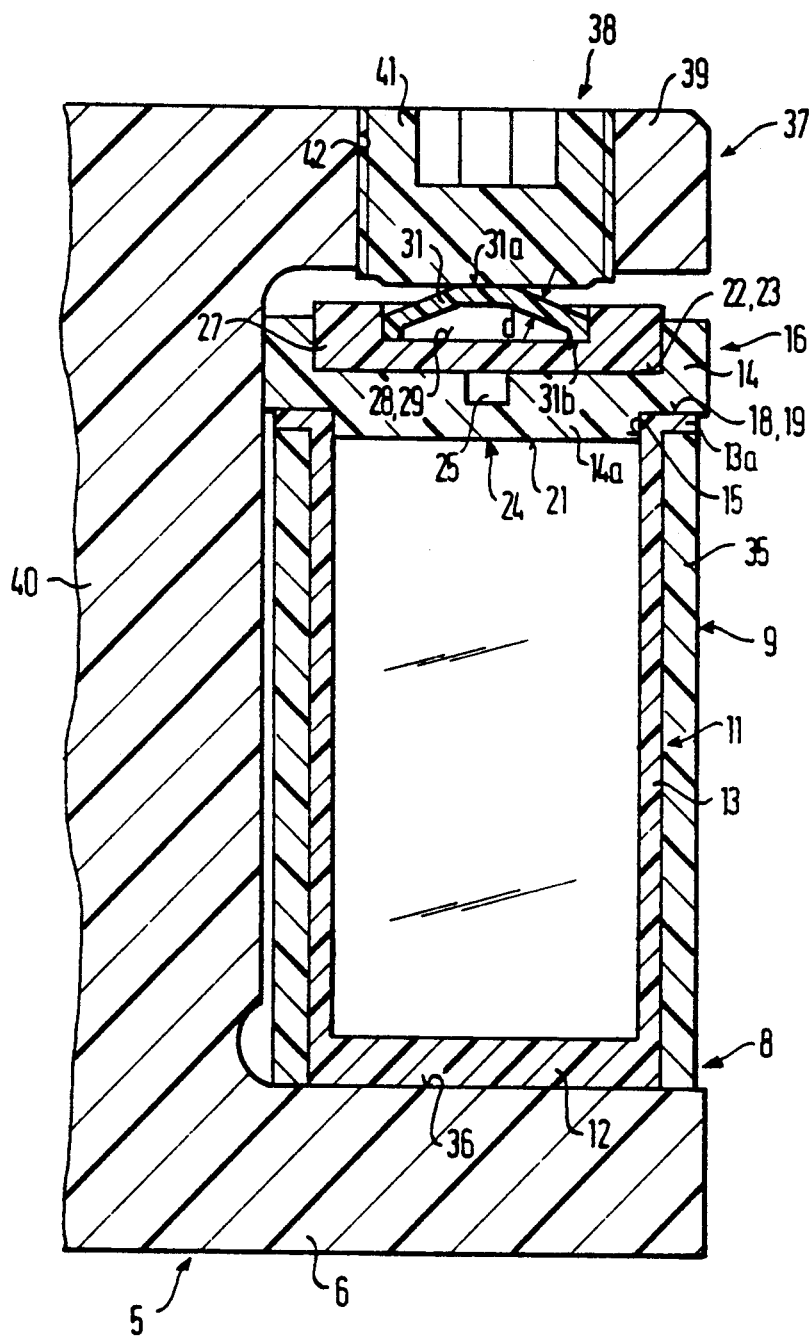
FIG. 2 shows on a larger scale a radial vertical partial section through the carrier in the region of a position for standing a sample holder.
Figure 3:
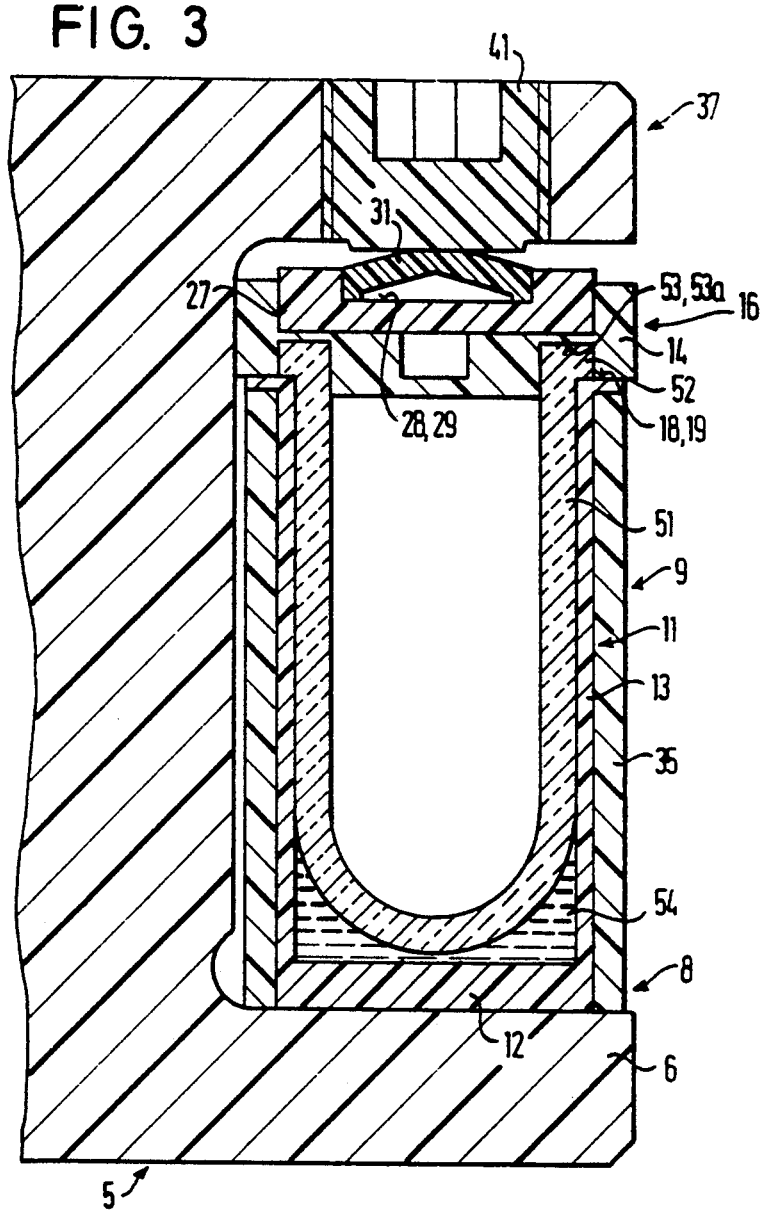
FIG. 3 and FIG. 4 show a partial section corresponding to FIG. 2 with a modified form of sample holder.
Figure 4:
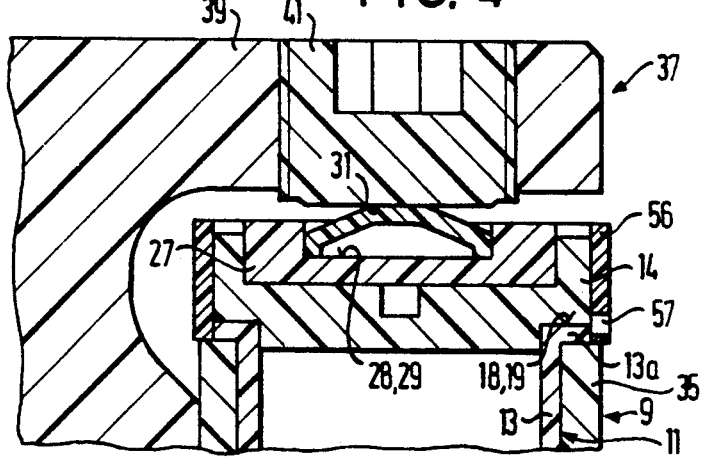

The thrust piece 31 may be a disc of solid elastic material or a body shaped as a plate spring such as a hollow, in particular dome-shaped, body, and is preferably an annular or closed plate spring In the embodiment shown in FIGS. 2 to 4 the plate-spring-shaped body is positioned so that it diverges downwards with its outer peripheral rim seated in the recess 28 with clearance or circumferential play therein.

The plate spring 31 is shaped as the frustum of a cone with a radially flat head 31a. Preferably the lower rim is also provided with a radial annular foot surface 31b. The tip of the space under the plate spring 31 may run to a point or it may be flattened. The flank wall is preferably of uniform thickness, cf. the thickness d. The plate spring 31 may be provided with a central hole and thus be annular, or it may be closed component. The plate spring 31 has a spring excursion of up to about 2 to 3 mm over which its prestressing force is or remains substantially the same.

The sample holder 9 consists of microwave-transparent and chemically inert material, in particular plastics material. A suitable material for the housing 11 and the lid is a heat-resistant plastic, preferably a polyfluoroethylene derivative, that is relatively soft, particularly at higher temperatures (PTFE, Teflon, TFA, PFA). The thrust piece 31 consists of a hard or viscoelastic plastic, preferably a HTC (high temperature compound) plastic such as a polyetherimide (PEI) or polyether-ether-ketone (PEEK). Alternatively it may consist of an elastomeric material such as, for example, silicone or Viton. The insert 27 consists of a hard plastic that provides the insert with high resistance to deformation and bending, particularly at different temperatures, and thus with high pressure stability The pressure stability and bending strength of the insert 27 is greater than the pressure stability of the plate spring. The same applies to a disc-shaped thrust piece of solid elastic material.

The pot-shaped housing 11 is preferably surrounded, preferably over its whole height, by a tubular protective case 35, to which it is firmly connected, for example by a force fit or adhesion. The protective case preferably consists of plastic having high rupture strength such as a polyetherimide (PEI) or polyether-ether-ketone (PEEK), for example of the same material as the plate spring 31, as previously described. The protective case 35 may be formed with an opening through which the temperature on the outer surface of the housing 11 can be measured by means of a temperature sensor in order to control the rotary drive of the carrier 5, the heating energy and/or the heating time of the microwave furnace.

For each of the sample holders 9 the carrier 5 has a bearing part that engages over the thrust piece 31 of the respective sample holder 9 when it is placed or stood in position on or in the carrier 5, so that the sample holder is held between the bearing part and the base surface 36 on the carrier 5 under a stress such that when the internal pressure in the sample holder 9 exceeds a predetermined value the lid 14 lifts against the stress and thus opens the valve 16. Preferably the bearing part, which is indicated generally by 37, is provided, coaxially with each of the sample holder positions 8, with a stressing device 38 by means of which the prestressing of the valve 16, which is predetermined by the resilience of the elastic thrust piece 31, may be effected.

In the present embodiment the bearing part 37 is a preferably circular upper flange or disc 39 of the carrier 5 that is connected to the lower plate 6 by a vertical shaft 40, for example integrally or by means of screws (not shown). Coaxially above each sample holder position 8 an externally threaded setting screw 41 is screwed into a corresponding vertical threaded hole in the upper flange or disc 39. The lower end of the setting screw 41 projects slightly downwards from the bottom surface of the upper flange or disc 39. At its upper end the setting screw 41 is provided with a tool-engaging element, for example an internal or external hexagon.

In the operating position the setting screw 41 is located coaxially above the lid 14 and the thrust piece 31. By tightening the setting screw 41 the thrust piece 31 and the lid 14 are forced downwards against the housing 11 to produce a definite pressure. The arrangement may be such that in the tightened position the setting screw 41 comes up against a stop: for example, the screw may have a head that meets the upper flange or disc 39.

To set particular desired prestressing forces or opening pressures for the valve 16 a corresponding number of thrust pieces 31 may be provided for each sample holder 9, these thrust pieces having an elasticity or resilience that is correspondingly different and adapted to the respective desired opening pressure.

In order to give each sample holder 9 a definite position in the carrier 5 a recess 45 is provided at each holder position 8. This recess is preferably open radially outwards so that the sample holder 9 concerned can conveniently be pushed in from the side. At least in its inner part the recess 45 is so shaped and/or adapted to the cross-sectional shape of the sample holder 9 that this is centered in the correct position.

The carrier 5 can be rotated about the axis of rotation 7 by a drive (not shown) so that the sample holders 9 are uniformly heated.

If it is desired to prevent contamination of the heating chamber 2 of the heating appliance 1 the carrier 5 may be provided with a protective housing 46, indicated in outline, that can preferably be slipped over the carrier 5 from above. Preferably the peripheral wall of the lower plate 6 is narrowed by an upwardly-facing step 47 to form a rim on which the protective housing 46, which may be bell-shaped, can stand. The protective housing 46 preferably consists of transparent material such as glass or plastic, so that the sample holder 9 and if desired also its reaction on heating is visible from outside.

For safety the carrier 5 and the plate 6 and/or flange or disc 39 may also be arranged so that the respective bearing part and/or at least one of the two plate 6 and flange or disc 39 can bend slightly outwards elastically or yield elastically under the opening pressure exerted upwards by the respective sample holder 9 when in use. In this way these parts perform a secondary opening function for the valve 16, to ensure that the valve 16 opens if the internal pressure is exceeded by more than the normal amount.

The carrier 5 and/or the plates 6, and flange or disc 39 also consist of plastic material. The additional opening function just described is assisted if the heat of reaction is transmitted to the plate 6 and flange or disc 39 and the plastic material thereof is softened and its strength is reduced, so that one or other of the plate 6 or the flange or disc 39 can bend outwards. Preferably the heat-resistance of this plastic is less than that of the protective case 35 and/or of the thrust piece 31, so that this plastic melts sooner. To avoid premature deformation of the plate 6, the bottom 12 of the housing 11 is made thicker than its wall 13 for the purpose of thermal insulation.

The setting screw 41 preferably likewise consists of plastic, namely of a hard plastic, to prevent the plate spring pressing into the setting screw 41.

When the pressure in the sample holder increases as the sample material is decomposed, the pressure on the lid at first increases, since the plastic of the container expands. When the internal pressure produces a force acting on the lid 14 from the inside that exceeds the resilience of the thrust piece 31, the opening pressure is reached and the lid 14 lifts up slightly while remaining parallel and the internal pressure is released between the surfaces 18, 19 of the sample holder 9.

In the embodiment shown in FIG. 3, in which the same reference numerals are used for similar parts, an inner container 51 consisting preferably of quartz is provided as an additional component that can be inserted loosely into the housing 11 from above and has a flange projection 52 on its rim with which in its inserted position it lies on the rim surface 18 of the housing 11. In this embodiment the lid 14 has an annular groove 53 to receive the rim or flange projection 52 of the inner container 51, so that the centering is maintained by means of a centering projection of the lid 14 that fits into the inner container 51 and the sealing surface 19 of the lid 14 still rests on the rim surface 18 of the housing 11 to ensure sealing of the sample holder 9. Here the bottom surface 53a of the annular groove functions as a sealing surface for the inner container by bearing tightly thereon. The bottom of the inner container 51 is preferably hemispherical so as to be free from bending forces arising from the internal pressure. The inner container 51 can therefore be made of fragile material, in particular quartz. Quartz is particularly suitable since it is chemically inert and transparent to microwaves, and also provides significant heat insulation.

The hollow cylindrical inner container 51 has a smaller internal diameter than the housing 11, with the result that the effective horizontal internal cross-sectional area is smaller. Consequently for the same opening pressure there is a smaller opening force acting on the lid 14, and the valve 16 and the lid 14 will only open at a higher internal pressure and consequently at a higher reaction temperature. By using the inner container 51 the user can thus obtain a correspondingly higher reaction pressure and higher reaction temperature with the use of the same thrust piece 31.

In order to increase the load limit, particularly when using an inner container 51 of fragile material such as quartz, it is advantageous to introduce a liquid, in particular water, into the space 54 between the bottom of the inner container 51 and the bottom of the housing 11. The water is heated by the microwave radiation and by the heat given off by the inner container 51 and accordingly generates a vapour pressure that can amount to as much as about 60 bar. In the present embodiment the plate spring forming the thrust piece 31 produces a closure force of about 10 000 N (1000 kPa), so that the valve 16 opens at an internal pressure of about 110 bar. If however the user wishes to operate with a lower internal pressure of e.g. 60 bar and a correspondingly lower temperature, he can use the sample holder 9 without its inner container 51.

In the embodiment shown in FIG. 4, in which the same reference numerals are used for similar parts, the joint between the rim surface 18 of the housing 11 and the sealing surface 19 of the lid 14 is covered radially outside by a guard ring 56 which surrounds the continuous peripheral joint closely or with a slight clearance. A radial opening 57 is provided through the guard ring 56 with its middle axis approximately level with the joint. Alternatively a plurality of holes 57 may be provided, distributed around the periphery. In the embodiment shown in FIG. 4 the guard ring 56 is a separate component that can be pushed over the lid 14 and over the rim flange 13a from above with clearance, so that the guard ring 56 rests on the upper rim surface of the protective case 35, the diameter of which is rather greater than that of the lid 14 and the rim flange 13a, which in the present case are the same size. The guard ring 56 likewise consists of a microwave-transparent and chemically inert plastic, preferably of the same plastic as the lid 14 and the housing 11 (PTFE derivative).

Another possibility is to provide the guard ring 56 with an internal flange on its upper rim, with which it can rest on the upper side of the lid 14. With this arrangement the guard ring 56 does not have to rest on the protective case 35, which can then be made smaller or thinner. It is also within the scope of the invention to form the guard ring 56 integrally on the outer rim of the rim flange 13a of the housing 11 or on the upper rim of the protective case 35, projecting upwards from these parts. It is also possible to form the guard ring 56 on the periphery of the lid 14 so that it projects downwards therefrom.

What is claimed is:

1. A sample holder for decomposition or analysis of sample material in a heating appliance, said sample holder comprising a receiving part having an upper peripheral rim which defines a filling opening for receiving sample material and which also forms a valve seat, a lid which has a resistance to deformation and bending for closing the receiving part at the filling opening, a moveable valve member formed on one side of said lid, said valve member being configured to close on said valve seat and an elastically yielding thrust piece formed by a plate spring with a dome shaped body having flanks and which diverges to an outer peripheral rim, said thrust piece being positioned to press elastically against said lid on the side thereof opposite said valve seat.

2. A sample holder according to claim 1 wherein the valve seat is situated at the upper peripheral rim of said filling opening, and wherein the valve member is formed by the lid and rests loosely on the upper peripheral rim.

3. A sample holder according to claim 1, wherein the valve member is a flat plate.

4. A sample holder according to claim 1, wherein the thrust piece has a first dimensional stability and wherein an insert having a second dimensional stability is provided between the valve member and the thrust piece, said second dimensional stability being greater than said first dimensional stability.

5. A sample holder according to claim 4, wherein said valve member has a third dimensional stability and wherein said third dimensional stability is less than said second dimensional stability.

6. A sample holder according to claim 1 wherein the dome shaped body of the plate spring diverges towards the lid.

7. A sample holder according to claim 1 wherein the thrust piece has a center and a radial head surface at said center and a radial annular foot surface at said outer peripheral rim.

8. A sample holder according to claim 4, wherein the thrust piece and the insert consist of microwave-transparent and chemically inert material.

9. A sample holder according to claim 1, wherein a rated break point is provided in the valve member.

10. A sample holder according to claim 1, wherein said receiving part includes an inner container of microwave-transparent and chemically inert material and having a rim extending upwards as far as the lid.

11. A sample holder according to claim 10, wherein said rim of said inner container has an outwardly-projecting flange which rests on a shoulder on said rim of the receiving part, and wherein an annular groove to receive the projecting flange is formed in said one side of the lid.

12. A sample holder according to claim 10 wherein said inner container has a hemispherical bottom.

13. A sample holder according to claim 1, wherein valve surfaces between the receiving part and the lid are formed by a radially extending rim surface of the receiving part and an opposing annular surface on said one side of the lid, and a guard ring surrounding said surfaces, said guard ring being of microwave transparent and chemically inert material.

14. A sample holder according to claim 13, wherein the guard ring is provided with means defining at least one opening at the level of the valve surfaces.

15. A sample holder according to claim 1, wherein said plate spring is made of a microwave-transparent and chemically resistant plastic material.

16. A sample holder according to claim 1, wherein said valve seat is situated at an edge portion of said filling opening and wherein said lid is formed with a centering projection which fits inside the filling opening.

17. A sample holder according to claim 1, wherein said valve seat is located at the rim of said receiving part and wherein said valve member is formed as part of said lid.

* * * * *